United States Patent [19]

Moehrle

[11] 4,108,180

[45] Aug. 22, 1978

[54] REUSABLE TAMPON

[76] Inventor: Doris B. Moehrle, P.O. Box 261, Southbridge, Mass. 01550

[21] Appl. No.: 752,602

[22] Filed: Dec. 20, 1976

[51] Int. Cl.² .............................................. A61F 13/00
[52] U.S. Cl. ................................ 128/285; 128/132 R; 128/296
[58] Field of Search ................... 128/270, 285, 132 R, 128/296, 294, DIG. 25

[56] References Cited

U.S. PATENT DOCUMENTS

| 969,640 | 9/1910 | Langstaff | 128/270 |
|---|---|---|---|
| 1,887,520 | 11/1932 | Spielberg et al. | 128/270 |
| 1,977,133 | 10/1934 | Linard | 128/285 |
| 2,188,923 | 2/1940 | Robinson | 128/285 |
| 3,794,029 | 2/1974 | Dulle | 128/285 |
| 3,812,856 | 5/1974 | Duncan et al. | 128/285 |
| 3,815,601 | 6/1974 | Schaefer | 128/285 |
| 3,902,493 | 9/1975 | Baier | 128/270 |

FOREIGN PATENT DOCUMENTS

| 961,247 | 1/1975 | Canada | 128/285 |
|---|---|---|---|
| 109,714 | 2/1944 | Sweden | 128/285 |

*Primary Examiner*—Lawrence W. Trapp
*Attorney, Agent, or Firm*—Salter & Michaelson

[57] ABSTRACT

A reusable tampon device including a body of flexible, dry compressible cellular sponge material such as polyurethane foam which is capable of absorbing body fluids such as menses and having an outer covering completely enclosing said body and comprising a porous structure having at least one open mesh fibrous material layer forming a bag and including a draw string interconnected with peripheral portions of the bag for opening and closing such to permit easy removal of the body therefrom for cleansing and reuse.

8 Claims, 4 Drawing Figures

REUSABLE TAMPON

BACKGROUND AND SUMMARY OF THE INVENTION

This invention relates to a tampon adapted for disposition in a human cavity, generally the female vagina and for the purpose of absorbing menstrual fluids. More particularly, the invention relates to an internally worn device which is of a dry compressible nature for insertion through the normally constricted vaginal opening for disposition into the vaginal cavity proper.

Devices of this very general nature are known and include those disclosed in U.S. Pat. No. 1,887,526 issued Nov. 15, 1932; U.S. Pat. No. 2,188,923 issued Feb. 6, 1940; U.S. Pat. No. 2,254,272 issued Sept. 2, 1941; U.S. Pat. No. 2,298,752 issued Oct. 13, 1942; and U.S. Pat. No. 3,794,029 issued Feb. 26, 1974. Despite the availability of articles such as those above disclosed the need exists for a tampon device which can be readily reused and yet of such a straightforward and simple nature so that it is of low enough cost to be alternatively discarded after each use, if desired. It is accordingly an object of the present invention to provide a device of this nature which not only can be conveniently reused, but which may conveniently be removed from the vagina by means of an interconnected drawstring forming a part thereof, and which drawstring can be used to temporarily manipulate and handle the device after using for subsequent washing and reuse in such a manner as to obviate contact with the soiled areas thereof.

Further desirable features for incorporation into devices of this nature are ease in insertion into the vagina in a comparatively dry state and the ability to absorb comparatively large quantities of menstrual fluid before becoming completely absorbed in order that the time interval for required replacement is not inconveniently short. Accordingly, a further object of the present invention is the provision of a device of the character described comprising a dry, compressible, highly absorbent, sponge-like material, the size of which can be additionally altered to provide various reservoir capacities to accomodate either light or heavy menstrual flows.

A still further object of the present invention is the provision of a device of the above-indicated nature which can be additionally used as a birth control mechanism as through its intended disposition in the vaginal cavity so as to effectively block the necessary upstream passage of semen therein.

These and other objects of the invention which will become more apparent hereinafter are met by the novel tampon construction of the present invention in the form of a resilient foam sponge body of a suitable non-toxic material encased or covered by a fibrous gauze material or the like which in turn comprises a completely enveloping bag for such body, the body and bag assembly being freely and comfortably insertable through the entrance on the vagina for disposition therein. The device further includes a drawstring to enable the fibrous bag to be opened and closed as for access to the absorbent body contained therein, which drawstring is adapted to extend outwardly from the bag and through the vaginal opening so as to form means for withdrawing the device from the vagina after passage of body fluids through the bag and absorption by said body.

Other objects, features and advantages of the invention will become apparent as the description thereof proceeds when considered in connection with the accompanying illustrative drawings.

DESCRIPTION OF THE DRAWINGS

In the drawings which illustrate the best mode presently contemplated for carrying out the present invention.

DESCRIPTION OF THE INVENTION

Figure 1:
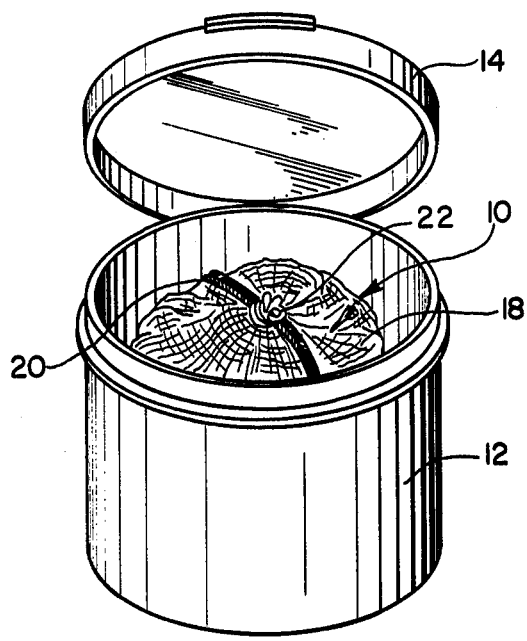
FIG. 1 is a perspective view of a tampon device in a dry ready-for-use state contained within a suitable container so that the device may be conveniently carried.

Turning now to the drawing and particular FIG. 1 thereof, the device 10 of the present invention in dry compressed form is shown within a container 12 having a cover 14. The container forms the means by which the device 10 may be conveniently carried on one's person, i.e. within a purse or the like. The cover 14 preferable forms a seal with the container 12 so as to form a fluid-tight barrier therewith in those cases, as will hereinafter be more fully explained, where it may be necessary to temporarily transport the device 10 after use. In this manner then the container serves to keep the device in clean condition prior to use and subsequent reuses and to additionally form the means by which the device, after absorbing body fluids, may be temporarily transported.

Figure 2:
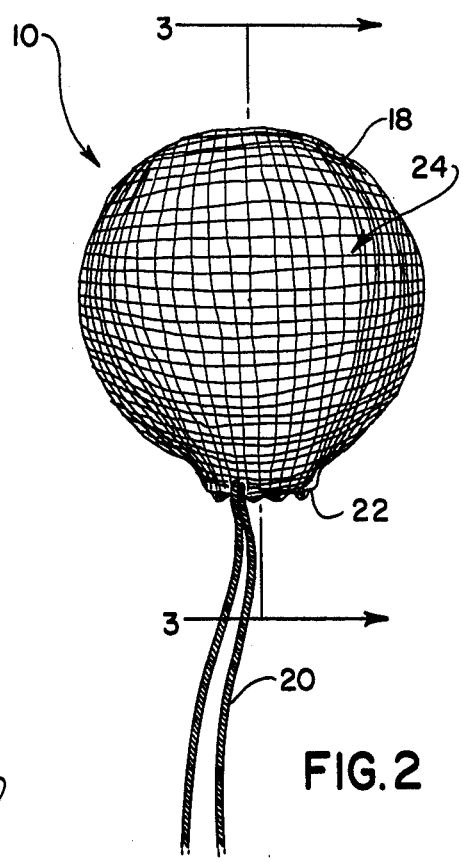
FIG. 2 is an elevational view of the device of the present invention wherein the bag structure thereof is shown in its closed operative condition.
Figure 3:
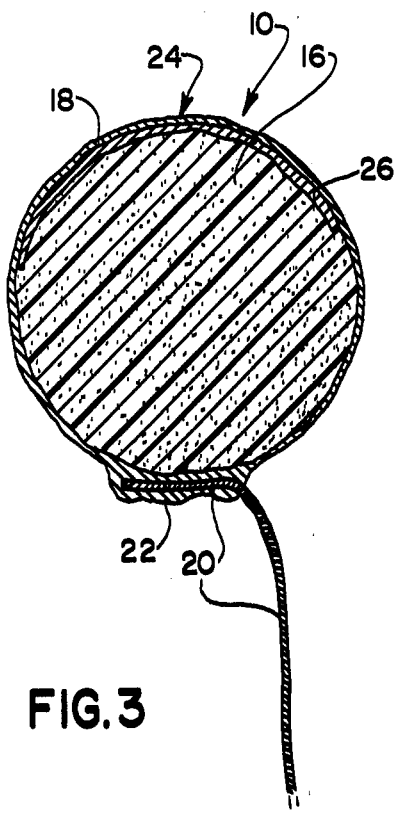
FIG. 3 is a sectional view taken along the line 3—3 of FIG. 2 showing in somewhat stylized form the cross-sectional configuration of the enveloping bag and its attached drawstring.
Figure 4:
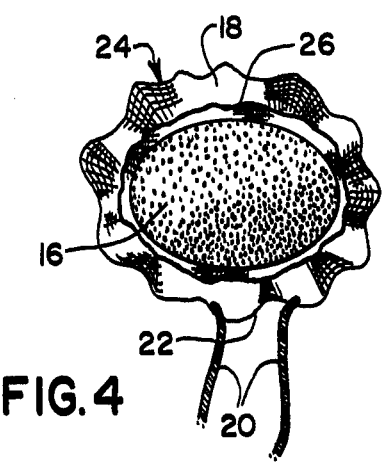
FIG. 4 is a perspective view showing the bag of the present invention in an open generally flat disposition thereby exposing the interior absorbent sponge body as in pre-use assembly thereof.

As best depicted in FIG. 4 of the drawing, the device 10 includes a body 16 of nontoxic, body fluid absorbable material such as a cellular plastic material such as polyurethane foam, and a layer of fibrous textile material 18 such as gauze and the like. The fibrous layer 18 has an open mesh structure and is preferable adapted to generally lie flat in its open disposition as shown in FIG. 4. The fabric layer 18 is further provided at peripheral portions thereof with a drawstring 20 which passes sinuously under, over and through the open mesh portions thereof in such a manner so that when the drawstring 20 is pulled tightly, it serves to draw the peripheral portions of the fabric layer 18 into a tightly closed, often random overlapping disposition with each other, as indicated by the fabric bunch 22 shown in FIGS. 2 and 3. The drawstring 20 is adapted for outward disposition from the bunch 22. In this manner then, the fabric layer 18 serves when in closed disposition, to form a bag 24 which completely envelops the fluid absorbable body 16.

It is important that the material forming the body portion 16 be compressible in a dry or at least partially dry state so that it can progressively, as by squeezing, be forced into the normally restrictive opening of the vagina so that upon disposition within the vaginal cavity proper it will assume a normally enlarged attitude and at least partially contact vaginal wall portions. Such attitude assures that menstrual fluid emerging from the upstream disposition of the cervix will contact the device 10 and be absorbed thereby. It should also be apparent then in such use position that the drawstring 20 is of a length so as to enable such to protrude outwardly from the vaginal orifice and thus serve as a means by which the device can be progressively urged through and outward of the vaginal cavity after having absorbed menstrual fluids. Furthermore, the open and preferably flat configuration of the fabric layer 18 enables various size sponge bodies 16 to be interchangeably used in combination therewith so that small or less absorbent bodies 16 may be used when light menstrual fluid flow is anticipated and larger or more highly absorbent bodies 16 utilized when a more heavy flow is anticipated. The completely open flat disposition of layer 18 facilitates such interchangeability of various body portions and eliminates both any need for more costly preformed bags or for a variety of different sized bags.

Removal and subsequent manipulation of the device 10 may as above indicated be facilitated by the drawstring 20 without need for contacting soiled portions thereof. The device may then be washed in a hand basin, comode, bidet or other sanitary facility to remove the absorbed fluid therein and thereafter, if desired, sterilized by water boiling. It should also be brought out that in order to enable such sterilization by boiling that the several materials utilized in the device must be able to withstand such conditions. In this regard it has been found that the polyurethane foam forming the body 16 satisfactorily meets such requirements although it should be clear that other materials able to withstand boiling and which have the necessary absorptive capabilities may alternatively be utilized.

After removal of any remaining liquid the device may be reinserted into the container 12 for its next periodic use or may after excess liquid removal be reinserted into the vaginal cavity for continued absorption of further menstrual flow. In such latter instance sterilization through boiling would normally be omitted.

Also in some cases, as when using foam materials which are somewhat harsh or dry to the touch or which may crumble when dry, it may be desirable to slightly premoisten the device prior to its insertion. In any event, however, the integrity of the body 16 is maintained by the close envelopment of the bag therearound. Furthermore, the bag 24 serves as a convenient mechanism whereby the body 16 may be washed free of menstrual fluid, it being clear that its open mesh structure is such to enable the clear passage of fluid therethrough and into contact with the absorbing body 16. In this regard it should be pointed out that portions of the bag 24 may be randomly or loosely enveloped about the body 16 or that overlapping folds of material 18 or the like may be disposed on the surface of the device and that such disposition additionally serves to hold, entangle or otherwise capture viscous portions of body fluids such as mucous and clotted or partially clotted whole blood particles which are commonly found in menstrual fluid. It should also be pointed out that such mesh structure and surface disposition may further serve to entrap seminal fluids which may enter from downstream portions of the vagina while the device 10 is in disposition threreabove and accordingly form a means by which sperm is prevented from moving upstream within such cavity and accordingly may also serve as a birth control device. When so utilized as a birth control device, a plurality of fibrous layers are preferably provided, which layers may be interfolded portions of a single layer and further preferably exhibit randomly outwardly loose fibrous mesh portions to increase contact with upstream directed seminal fluids.

When used for its primary function to absorb menstrual fluids, the pad or body 16 of the device 10 is preferably capable of progressive expansion upon absorbing fluid. It should be noted that such expanstion is unrestrained by the bag structure 24 inasmuch as the drawstring 20 thereof is untied and free so as to permit preipheral expansion to accomodate enlargement of the bag and is also free to be drawn upwardly into the vaginal cavity to afford such bag expansion. Furthermore, the interfolded or bunched structure 22 present at that portion of the device 10 proximal the drawstring 20 serves to provide a mesh covering in such location even after substantial bag expansion. In some cases when the bag 24 is in a partially or fully expanded state it may be desirable to provide an additional fabric layer 26 over those portions of the body 16 located away from the bunch 22 so as to assure an interfolded or plural thickness layer in such locations, where desirable. Such additional layer or layers 26 may be of same fabric material comprising layer 18 or of similar material so long as such is capable of withstanding the environment in which they will be utilized without adverse affect as through discoloration, premature wear loss of strength and the like. Additional fabric layers or layer may be similarly provided at the side of the body 16 proximal the bunch 22, particularly in those cases where the bunch 22 includes a generally central positioned secondary opening (not shown) therethrough. When not in use, the device 10 may be wrapped in a compressed state as by encircling wraps of the drawstring 20 about the central portions thereof as depicted in FIG. 1 of the drawing. This assures a tight compressed wrap for carrying convenience, such as in the container 12.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A reusable tampon device comprising a body of nontoxic, flexible, dry compressible menses absorptive material adapted for constrictive movement past the vaginal opening and for expanded conformation with wall portions of the vagina upstream of said opening, said body completely enveloped in an outer porous structure adapted to lie essentially flat in open relaxed disposition and forming a bag therefor and having at least one open mesh fibrous material layer, said bag in turn having an opening for receipt of said body and a draw string alternatively passing over, under and through said open mesh material along peripheral portions thereof to form said bag and for closing said opening so as to completely encompass said body therein and for opening said bag to permit removal of said body therefrom after use, said draw string adapted for outward extension from said bag and through said vaginal opening to form means for withdrawing said device from the vagina after passage of menses through said bag and absorption by said body when said device is in use and for at least partial circumferential envelopment of said body to compress the same when said device is not in use.

2. The device set forth in claim 1, said body adapted for placement generally centrally of said mesh material in said open flat disposition thereof, at least the top portions of said body being further covered by an additional open mesh fibrous layer.

3. The device set forth in claim 1, said fibrous layer being bunched together by the closing action of said draw string to form multiple layer thickness proximal the extension of said draw string from said bag.

4. The device set forth in claim 3, said body having a further open mesh fibrous layer disposed on surface portions of said body positioned distal from said layer bunch.

5. The device as set forth in claim 1, said open porous structure including a plurality of open mesh fibrous material layers disposed about said body.

6. The device as set forth in claim 1, portions of said open mesh layer loosely disposed to present random outwardly extending fibrous mesh portions for surface retention of high viscosity body fluids such as mucous, clotted blood and semen.

7. The device as set forth in claim 1, said bag being generally circular in said flat disposition.

8. The device as set forth in claim 1, wherein said body is formed of an open cell polyurethane foam.

* * * * *